(12) United States Patent
Zimmerling et al.

(10) Patent No.: US 7,976,453 B2
(45) Date of Patent: Jul. 12, 2011

(54) REDUCING EFFECT OF MAGNETIC AND ELECTROMAGNETIC FIELDS ON AN IMPLANT'S MAGNET AND/OR ELECTRONICS

(75) Inventors: Martin Zimmerling, Patsch (AT); Erwin Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1 day.

(21) Appl. No.: 12/498,095

(22) Filed: Jul. 6, 2009

(65) Prior Publication Data
US 2010/0004716 A1 Jan. 7, 2010

Related U.S. Application Data

(60) Continuation of application No. 11/475,705, filed on Jun. 27, 2006, now Pat. No. 7,566,296, which is a continuation of application No. 10/994,950, filed on Nov. 22, 2004, now Pat. No. 7,091,806, which is a division of application No. 10/405,093, filed on Apr. 1, 2003, now Pat. No. 6,838,963.

(60) Provisional application No. 60/369,208, filed on Apr. 1, 2002, provisional application No. 60/387,455, filed on Jun. 10, 2002.

(51) Int. Cl.
*H04R 25/00* (2006.01)
*H01F 7/02* (2006.01)
(52) U.S. Cl. ............... 600/25; 600/12; 607/55; 607/57; 335/305; 335/306
(58) Field of Classification Search .......... 600/12, 600/25; 607/55–57; 335/302–306
See application file for complete search history.

(56) References Cited

U.S. PATENT DOCUMENTS
3,487,403 A 12/1969 Pihl ............................ 340/373
(Continued)

FOREIGN PATENT DOCUMENTS
EP 2031896 4/2009
(Continued)

OTHER PUBLICATIONS

MD, Ph.D., Hobbs, et al, "Magnetic Resonance Image—Guided Proteoics of Human Glioblastoma Multiforme", *Journal of Magnetic Resonance Imaging*; pp. 530-536 (2003).

(Continued)

*Primary Examiner* — Ramon M Barrera
(74) *Attorney, Agent, or Firm* — Sustein Kann Murphy & Timbers LLP

(57) ABSTRACT

An implantable magnet that can freely turn in response to an external magnetic field, thus avoiding torque and demagnetization on the implantable magnet. The implantable magnet can be combined with an electric switching function depending on the orientation of an external magnetic field, thus protecting an implanted coil and/or implant electronics against induction of over-voltage or performing an electric switching function for other various purposes. The magnetic switch may further include, for example, a first switching contact and a second switching contact. A magnetically soft body that includes an electrically conductive surface is shiftable between a first position where the body is in simultaneous contact with the first and second switching contacts, and a second position where the body is out of contact with at least one of the first and second switching contacts. The body and the implantable magnet are positioned such that the body is shifted to one of the first position and the second position as a function of the external magnetic field resulting in a magnetic force between the magnet and the magnetically soft body.

18 Claims, 11 Drawing Sheets

U.S. PATENT DOCUMENTS

| | | | | |
|---|---|---|---|---|
| 3,573,812 | A | 4/1971 | Pihl | 340/373 |
| 3,801,767 | A | 4/1974 | Marks | 200/161 |
| 3,987,967 | A | 10/1976 | Kuznetsov et al. | 241/1 |
| 4,038,990 | A | 8/1977 | Thompson | 128/419 PG |
| 4,199,741 | A | 4/1980 | Serrus Paulet | 335/206 |
| 4,257,936 | A | 3/1981 | Matsumoto et al. | 524/413 |
| 4,317,969 | A | 3/1982 | Riegler et al. | 200/52 R |
| 4,596,971 | A | 6/1986 | Hirabayashi et al. | 335/205 |
| 4,628,907 | A | 12/1986 | Epley | 128/1.6 |
| RE32,947 | E | 6/1989 | Dormer et al. | 128/420.6 |
| 4,868,530 | A | 9/1989 | Ahs | 335/207 |
| 4,918,745 | A | 4/1990 | Hutchison | 455/41 |
| 5,015,224 | A | 5/1991 | Maniglia | 600/25 |
| 5,183,056 | A | 2/1993 | Dalen et al. | 128/782 |
| 5,456,654 | A | 10/1995 | Ball | 600/25 |
| 5,624,376 | A * | 4/1997 | Ball et al. | 600/25 |
| 5,630,835 | A | 5/1997 | Brownlee | 607/60 |
| 5,716,407 | A | 2/1998 | Knapp et al. | 623/11 |
| 5,749,912 | A | 5/1998 | Zhang et al. | 607/57 |
| 5,800,336 | A | 9/1998 | Ball et al. | 600/25 |
| 5,857,958 | A | 1/1999 | Ball et al. | 600/25 |
| 5,877,664 | A | 3/1999 | Jackson, Jr. | 335/205 |
| 5,897,486 | A | 4/1999 | Ball et al. | 600/25 |
| 6,040,762 | A | 3/2000 | Tompkins | 340/426 |
| 6,175,767 | B1 | 1/2001 | Doyle, Sr. | 607/57 |
| 6,178,079 | B1 | 1/2001 | Renger | 361/118 |
| 6,178,353 | B1 | 1/2001 | Griffith et al. | 607/61 |
| 6,190,305 | B1 | 2/2001 | Ball et al. | 600/25 |
| 6,208,235 | B1 | 3/2001 | Trontelj | 340/10.1 |
| 6,217,508 | B1 | 4/2001 | Ball et al. | 600/25 |
| 6,219,580 | B1 | 4/2001 | Faltys et al. | 607/57 |
| 6,263,230 | B1 * | 7/2001 | Haynor et al. | 600/424 |
| 6,292,678 | B1 | 9/2001 | Hall et al. | 600/374 |
| 6,295,472 | B1 | 9/2001 | Rubinstein et al. | 607/55 |
| 6,313,551 | B1 | 11/2001 | Hazelton | 310/12 |
| 6,348,070 | B1 | 2/2002 | Teissl et al. | 623/11.11 |
| 6,358,281 | B1 | 3/2002 | Berrang et al. | 623/10 |
| 6,401,723 | B1 * | 6/2002 | Garibaldi et al. | 128/899 |
| 6,505,062 | B1 | 1/2003 | Ritter et al. | 600/407 |
| 6,506,987 | B1 | 1/2003 | Woods | 290/61.62 |
| 6,522,909 | B1 | 2/2003 | Garibaldi et al. | 600/424 |
| 6,838,963 | B2 | 1/2005 | Zimmerling et al. | 335/205 |
| 7,091,806 | B2 | 8/2006 | Zimmerling et al. | 335/207 |
| 7,566,296 | B2 | 7/2009 | Zimmerling et al. | 600/25 |
| 2003/0120202 | A1 * | 6/2003 | Gordon | 604/28 |
| 2004/0012470 | A1 | 1/2004 | Zimmerling et al. | 335/205 |
| 2005/0062567 | A1 | 3/2005 | Zimmerling et al. | 335/150 |
| 2006/0244560 | A1 | 11/2006 | Zimmerling et al. | 335/207 |

FOREIGN PATENT DOCUMENTS

| | | |
|---|---|---|
| GB | 1468890 | 3/1977 |
| JP | 04/023821 | 1/2004 |
| SU | 1690749 | 11/1991 |
| WO | WO 97/32629 | 9/1997 |
| WO | WO 00/10361 | 2/2000 |
| WO | WO 03/036560 | 5/2003 |
| WO | WO 03/081976 | 10/2003 |
| WO | WO 03/092326 | 11/2003 |
| WO | WO 2004/114723 | 12/2004 |

OTHER PUBLICATIONS

International Searching Authority, International Search Report (Nov. 28, 2003).

Heller et al, "Evaluation of MRI Compatibility of the Modified Nucleus Multichannel Auditory Brainstem and Cochlear Implants", *The American J. of Otology* 17(5); pp. 724-729 (Sep. 1996).

Teissl et al, "Cochlear Implants: In Vitro Investigation of Electromagnetic Interference at MR Imaging—Compatibility and Safety Aspects", *Radiology* 208(3); pp. 700-708 (Sep. 1998).

Teissl et al, "Magnetic Resonance Imaging and Cochlear Implants: Compatibility and Safety Aspects", *J. Magn. Reson. Imaging* 9(1); pp. 26-38 (Jan. 1999).

United States Patent and Trademark Office, Office Action dated Feb. 12, 2007, pertaining to U.S. Appl. No. 11/158,322, 6 pages.

Bromberg & Sunstein LLP, Response A filed May 14, 2007 to Office Action dated Feb. 12, 2007, pertaining to U.S. Appl. No. 11/158,322, 11 pages.

United States Patent and Trademark Office, Office Action dated Mar. 17, 2008, pertaining to U.S. Appl. No. 11/158,322, 14 pages.

Bromberg & Sunstein LLP, Response B filed Jun. 17, 2008 to Office Action dated Mar. 17, 2008, pertaining to U.S. Appl. No. 11/158,322, 10 pages.

Bromberg & Sunstein LLP, Response filed Sep. 19, 2008 to Office Action dated Jun. 26, 2008, pertaining to U.S. Appl. No. 11/671,132, 8 pages.

United States Patent and Trademark Office, Office Action dated Oct. 27, 2008, pertaining to U.S. Appl. No. 11/671,132, 7 pages.

Bromberg & Sunstein LLP, Response filed Jan. 5, 2009 to Office Action dated Oct. 27, 2008, pertaining to U.S. Appl. No. 11/671,132, 13 pages.

International Searching Authority, Invitation to Pay Additional Fees—International Application No. PCT/IB2004/002588, dated Dec. 12, 2004, 4 pages.

European Patent Office, European Search Report (Extended), dated Jun. 3, 2009, 8 pages.

\* cited by examiner

REDUCING EFFECT OF MAGNETIC AND ELECTROMAGNETIC FIELDS ON AN IMPLANT'S MAGNET AND/OR ELECTRONICS

CROSS REFERENCE TO RELATED APPLICATIONS

This application is a continuation of U.S. patent application Ser. No. 11/475,705, filed Jun. 27, 2006, which in turn is a continuation of U.S. patent application Ser. No. 10/994,950, filed Nov. 22, 2004, which issued as U.S. Pat. No. 7,091,806, which in turn is a divisional of U.S. patent application Ser. No. 10/405,093, filed Apr. 1, 2003, which issued as U.S. Pat. No. 6,838,963, which in turn claims the benefit of U.S. Provisional Patent Application No. 60/369,208, filed Apr. 1, 2002, and U.S. Provisional Patent Application 60/387,455, filed Jun. 10, 2002. Each of these references is incorporated herein by reference, in their entirety.

TECHNICAL FIELD

The present invention generally relates to a magnetic switch, and a method and apparatus for reducing the effect of magnetic fields and electromagnetic fields on an implanted magnet and electronics in an implant, respectively.

BACKGROUND ART

Partly implantable systems may use magnets to hold internal and external pieces in place. For example, as shown in FIG. 1, a cochlear implant 102 located under the skin 103 and embedded in bone 104 typically include a first magnet 106 placed in the center of the implant 102, and a coil 108. An external part 101 includes a second magnet 105 that is positioned over the first magnet 106 such that the external part 101 is held against the implant 102 in an optimum position. By maintaining such a position, an external coil 107 positioned inside external part 101 can, via inductive coupling, transmit a transcutaneous signal and/or power to the coil 108 of implant 102.

Upon a wearer of such a cochlear implant 102 having to undergo Magnetic Resonance Imaging (MRI) examination, interactions between the implanted magnet 106 and the applied external MRI magnetic field may, at higher field strength (i.e. above about 1 Tesla), produce two harmful effects. First, as shown in FIG. 2, the implanted magnet 202 may experience a torque that can twist the magnet 202 and the implant 201 out of position, thereby injuring the implant wearer, as shown in FIG. 2. Secondly, due to the external magnetic field, the implanted magnet may become partly demagnetized and may not be strong enough after the MRI field exposure to hold the external part in place.

Another potentially dangerous effect may occur when RF pulses emitted by the MRI unit induce voltages in the implant coil, implant circuit and/or electrode circuit. These voltages may generate unwanted stimulation, especially in implants with analog electronic circuitry. Additionally, over-voltages may be generated which could destroy the implant electronics.

Still other adverse effects can occur when a patient with a cochlear implant undergoes an MRI examination. For example, artifacts may appear in the MRI image. These artifacts are caused by the local magnetic field of the implanted magnet, which distorts the homogeneous MRI field.

Present efforts to address the above-described problems include generally forbidding a patient with the cochlear implant to undergo the high-field MRI examination. However, this may exclude the patient from certain important diagnostic measures. Alternatively, the implant can be designed to minimize certain risks related to MRI examinations. For example, to avoid risks related to the implant magnet, the implant could be designed in such a way that the magnet can be removed from the patient before MRI examination and be reinserted afterwards. This requires two surgical interventions in order to perform a MRI examination, and makes it impossible to use the implant system during the healing phase of the incision. Furthermore, the necessity to surgically remove the magnet before the MRI examination is a drawback especially in emergency cases and even could be forgotten in some cases. Other ways to minimize the risk of a torque exerted on the implant magnet is to use two identical implant magnets with opposite orientation, as described in U.S. Pat. No. 6,348,070 issued to Teissl and Hochmair, or to use a magnetically soft material (also called a "keeper") instead of a permanent magnet inside the implant. At present, the magnetically soft material used for the keeper has been limited to solid alloys or Ferrite.

Current methodologies to reduce the risks related to induction of possibly excessive voltages in the implant coil and circuits during an MRI examination include, for example, adding a Zener diode or a similar electronic component to the electronic circuit. Other designs include the use of two implant coils with opposite direction so as to reduce the induced voltages in the implant coils, and the use of REED contacts as described in U.S. Pat. No. 6,348,070 issued to Teissl and Hochmair.

SUMMARY OF THE INVENTION

In a first embodiment of the invention there is provided a magnetic switch. The magnetic switch includes a first switching contact and a second switching contact, and a magnet free to rotate such that the magnet is capable of aligning at least partially with an external magnetic field. A magnetically soft body that includes an electrically conductive surface is shiftable between a first position where the body is in simultaneous contact with the first and second switching contacts, and a second position where the body is out of contact with at least one of the first and second switching contacts. The body and magnet are positioned such that the body is shifted to one of the first position and the second position as a function of the external magnetic field resulting in a magnetic force between the magnet and the magnetically soft body.

In related embodiments of the invention, the magnet may, without limitation, be a sphere or cylindrical. The magnetically soft body may have a calotte having a curvature that follows an adjacent surface of the magnet. The switch may be enclosed in a housing, which may be non-magnetic. The switch may be hermetically encapsulated. The switch may be included in a cochlear implant, the implant further including a first coil adapted to be electromagnetically coupled with a second coil of an external device. The switch may provide overvoltage protection for the cochlear implant, as a function of an orientation of the external magnetic field.

In accordance with another embodiment of the invention, an implant includes a housing. At least one magnet is free to turn in the housing such that the at least one magnet is capable of aligning at least partially with an external magnetic field.

In related embodiments of the invention, the at least one magnet is adapted to be magnetically attracted to a non-implanted magnet of an external device so as to hold the external device in a desired position relative to the implant. The implant may be a cochlear implant. The implant may include a first coil adapted to be electromagnetically coupled with a second coil of an external device. The housing may be an encapsulation that hermetically seals the at least one magnet. The housing may include a magnetically soft material at least partially surrounding the at least one magnet. The housing may be made of titanium, nonmagnetic stainless steel, or a ceramic. The adjacent surfaces of the housing or magnet may be lubricated, or be made of Teflon. The at least one magnet may be spherical or cylindrical in shape and/or coated with a conductive surface. The at least one magnet may be a plurality of spherically shaped magnets.

In accordance with another embodiment of the invention, an implant includes a magnet adapted to be magnetically attracted to a non-implanted magnet of an external device so as to hold the external device in a desired position relative to the implant. A magnetically soft material at least partially surrounds the magnet so as to reduce the torque and/or demagnetization of the magnet caused by an external magnetic field. The implant may be a cochlear implant.

In accordance with another embodiment of the invention, a magnetic switch includes a housing and a first and second switching contact positioned within the housing. Additionally, a magnet is positioned within the housing. The magnet is free to rotate in the housing and includes at least one conductive surface covering a portion of the magnet. The magnet is capable of rotating, in response to an external magnetic field, to one of a first position and a second position. In the first position, the at least one conducting surface is in contact with both the first and second switching contacts. In the second position, the conducting surface is out of contact with at least one of the first and second switching contacts.

In related embodiments of the invention, the conducting surface covers a magnetic pole. The magnet may be substantially spherical. The magnet may include a recessed region, which may be non-conductive. The switch may be part of a cochlear implant. The cochlear implant may include a first coil adapted to be electromagnetically coupled with a second coil of an external device. The switch may provide overvoltage protection for the cochlear implant, as a function of an orientation of the external magnetic field.

In accordance with another embodiment of the invention, a magnetic switch includes a housing and at least one spring contact. Each contact includes a pin for driving the contact. A magnet is positioned in the housing and is free to rotate in the housing such that it is capable of aligning at least partially with an external magnetic field. The magnet further includes at least one recessed and/or grooved region. The magnet and the pin are positioned such that the magnet contacts and drive the pin when the pin is not aligned with one of the at least one recessed regions. The pin is not driven when the pin is aligned with one of the at least one recessed regions.

In related embodiments of the invention, at least one recessed region is positioned at a magnetic pole. The magnet may include a north pole and a south pole, the at least one recessed region positioned between the north pole and the south pole. The switch may be part of a cochlear implant, and may include a first coil adapted to be electromagnetically coupled with a second coil of an external device. The switch may provides overvoltage protection as a function of an orientation of the external magnetic field.

In accordance with yet another embodiment of the invention, an implant includes a housing. A magnet is positioned within the housing, the magnet free to rotate such that the magnet is capable of aligning at least partially with an external magnetic field. A magnetically soft body is coupled to the housing. The magnetically soft body is positioned adjacent the magnet so as to provide a path of low reluctance to the magnet.

In related embodiments of the invention, the magnet is one of a spherical magnet and a cylindrical magnet. The body may include a calotte shaped to fit the surface of the magnet. A lubricant may be placed between the magnet and the body. The magnet may include a Teflon surface. The magnet may be adapted to be magnetically attracted to a non-implanted magnet of an external device, so as to hold the external device in a desired position relative to the implant and such that the magnetically soft body is positioned between the magnet and the non-implanted magnet.

In accordance with another embodiment of the invention, an implant includes a housing. A volume of Ferrofluid is located within the housing, wherein the Ferrofluid becomes magnetized in the direction of an external magnetic field.

In related embodiments of the invention, the volume of Ferrofluid is adapted to be magnetically attracted to a non-implanted magnet of an external device, so as to hold the external device in a desired position relative to the implant. The implant may be a cochlear implant.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 3:
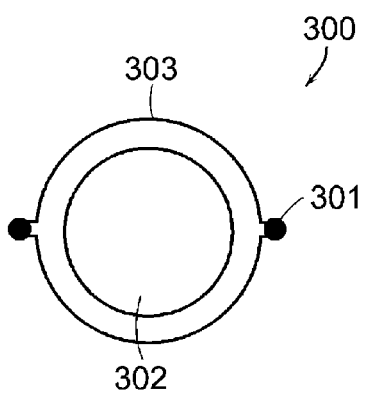
FIG. 3 is a graphical illustration of an implanted magnet encapsulated in a spherical shell, in accordance with one embodiment of the invention.

In illustrative embodiments of the invention, a method and device for reducing the effects of strong magnetic fields on an implanted magnet is presented. FIG. 3 shows an implant 300 for implementing an embodiment of the invention. The implant 300 includes a magnet 302 that is held in the implant 300 in such a way that the magnet 302 can turn into the direction of an externally applied magnet field. Thus, the magnet 302 does not experience any torque as a result of the external magnet field, nor will it become demagnetized.

The magnet 302 may be enclosed in a housing 303. The housing 303 allows the implanted magnet of whatever shape to turn, possibly with some restrictions, into the external magnetic field lines. In various embodiments of the invention, magnet 302 is hermetically encapsulated so as to prevent corrosion and/or leakage of the material into the body of the implant 300. Material used for the housing/encapsulation 303 may include, without limitation, titanium, nonmagnetic stainless steel, or ceramic. Housing 303 may be held together by a weld seam 301 after insertion of the magnet 302.

As shown in FIG. 3, magnet 302 is a spherical magnet that is free to turn in any direction. To minimize friction between the magnet 302 and the housing 303, a lubricant can be placed in the small gap between the magnet 302 and the housing 303. Alternatively, or in addition to the use of lubricant, the magnet 302 and/or the housing 303 may be coated by a thin layer of material to minimize friction, such as Teflon.

Instead of a spherical magnet 302, magnet 302 may be of a variety of shapes. For example, magnet 302 may be, without limitation, a cylinder that can rotate about its axis. The cylindrical magnet carries a magnetization being normal to its axis. This axis can be arranged horizontally parallel to the skin in the plane of the implanted coil. This allows the magnet to turn around its axis, so that it may turn its magnetic moment either towards the external holding magnet (as is typically the case during normal use) or so as to align with the field generated, for example, by a high field MRI scanner, whose field lines in a typical examination position run along the patient's axis. In a slightly different arrangement, the axis of the cylinder is still mounted in the plane of the implanted coil, but at approximately up to 45° off the horizontal plane to be able to partially adjust to (lower field) MRI-machines which use vertical magnetic fields. The advantage of a cylindrical magnet is that its aspect ratio (i.e. diameter vs. length) can be chosen such that for a given volume (which is necessary to generate an adequate holding force) the thickness of the magnet is smaller than that of a spherically shaped magnet.

Figure 4A:
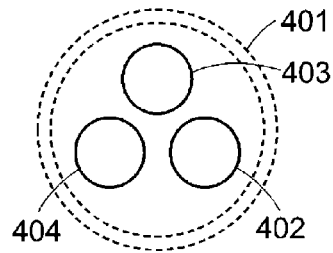
FIG. 4(a) is a graphical illustration of a top view of an implant that includes three free rotating spherical magnets, in accordance with one embodiment of the invention.

In accordance with an embodiment of the invention, the implant may include several smaller magnets instead of one magnet, allowing for a thinner design of the implant. For example, FIGS. 4 (a) and 4(b) show a top view and a side view, respectively, of an implant 401 that includes three spherically shaped magnets 402-404 and a coil 406. These magnets 402-404 may be arranged some distance apart from each other, thus facilitating the orientation of magnets 402-404 primarily along the field lines of an external holding magnet 405, as shown in FIG. 4(b).

Figure 1:
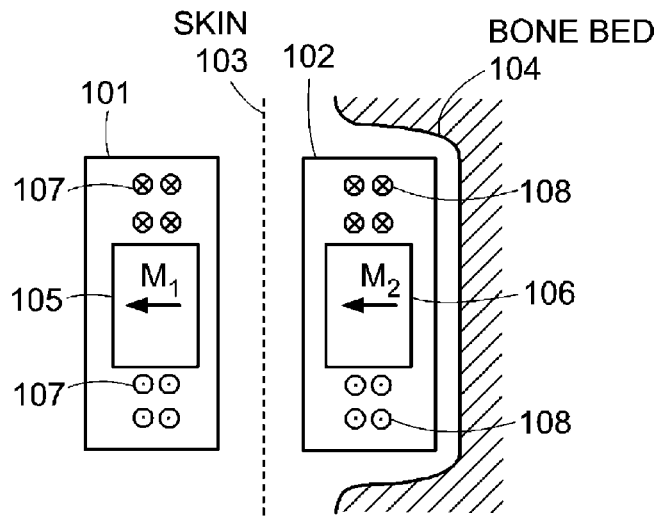
FIG. 1 is a graphical illustration of a cochlear implant with an external part held against the cochlear implant (PRIOR ART)
Figure 2:
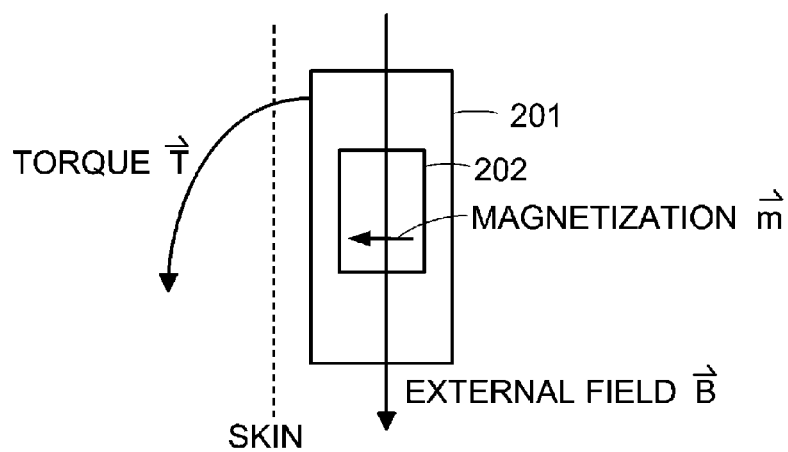
FIG. 2 is a graphical illustration of an implanted magnet of a cochlear implant experiencing a torque as a result of an external magnetic field (PRIOR ART)
Figure 4B:
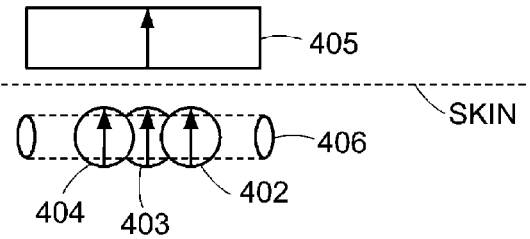
FIG. 4(b) is a graphical illustration of a side view of the implant of FIG. 4(a), in accordance with one embodiment of the invention.

As shown in FIGS. 1 and 4(b), both the implant and the external part held adjacent to the implant may have coils which are positioned across from each other. A signal, such as a radio frequency (RF) electrical signal, is inductively coupled to the implant so as to transfer required electrical power and or other signals. The RF signal may induce eddy currents in the implant magnet and/or the magnet of the external device. This can cause power losses for the implant system. In accordance with various embodiments of the invention, these power losses may be reduced by using an electrically conducting material, such as gold, for the coating and/or encapsulation of the implanted magnet(s) and/or external magnet(s). The coating acts as a short circuit for the incident RF wave, resulting in minimal power dissipation.

Figure 5A:
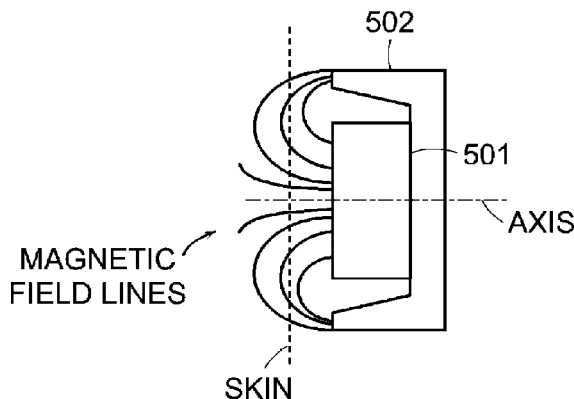
FIG. 5(a) is a graphical illustration of an implanted magnet embedded in magnetically soft matter, in accordance with one embodiment of the invention.
Figure 5B:
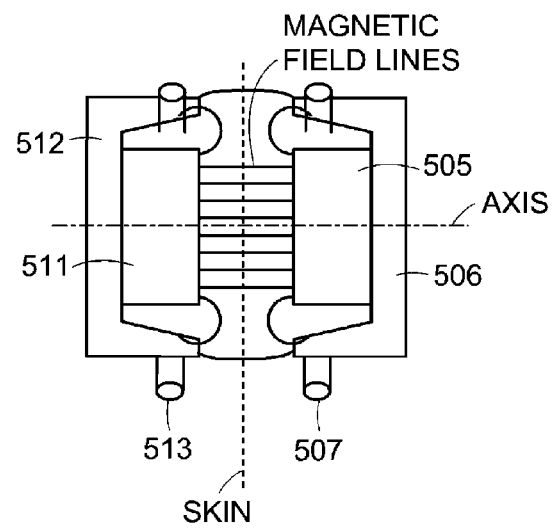
FIG. 5(b) shows the implant of FIG. 5(a) with an external part held against the implant, in accordance with one embodiment of the invention.

Another embodiment of the invention for reducing the effects of strong magnetic fields on an implanted magnet is shown in FIG. 5(a). The implanted magnet 501 is partially surrounded by magnetically soft material 502 which creates a low reluctance path for magnetic flux. This will partly shield the magnet 501 from the external magnetic field, reducing both the torque and the demagnetization of magnet 501 to a large extent. The magnetically soft material 502 may form, without limitation, a potlike shaped structure that includes a cavity in which the magnet 501 is positioned. The surface of the magnet 501 not covered by the magnetically soft material is typically orientated, and generates a magnetic field, normal to the skin. The magnetically soft material 502 may be, without limitation, highly permeable Ferrite, an alloy, or a Ferrofluid, which contains tiny magnetic particles suspended in fluid. FIG. 5(*b*) shows an external part 510 held in place by an implant 505, and the approximate magnetic field generated, in accordance with one embodiment of the invention. Both the implant 505 and the external part 510 include a magnet 506 and 511, a magnetically soft material 506 and 512, and a coil 507 and 513, respectively.

Figure 6A:
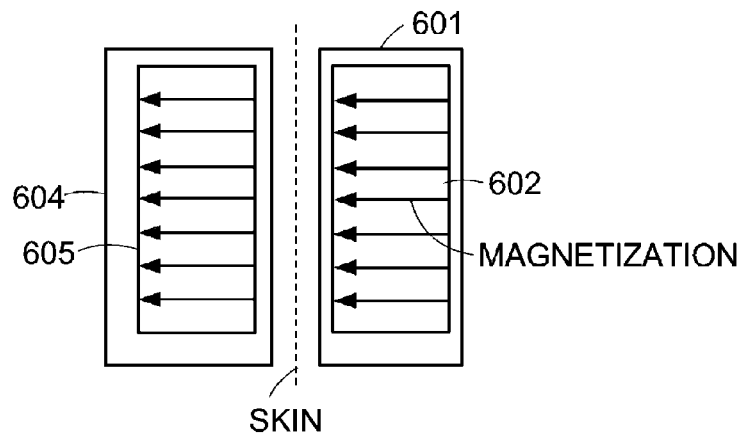
FIG. 6(a) is a graphical illustration of implant that includes Ferrofluid with an external part held against the implant, in accordance with one embodiment of the invention.
Figure 6B:
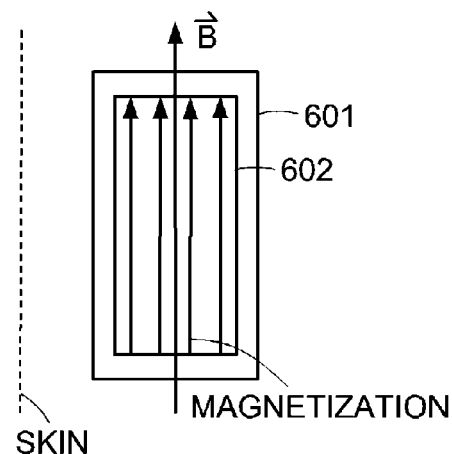
FIG. 6(b) shows the implant of 6(a) when immersed in an external magnetic field of a MR scanner, in accordance with one embodiment of the invention.

Referring back to FIG. 1 and as known in the art, magnet 106 may be a magnetically soft material (also known as a keeper). At present, the magnetically soft material used for the keeper has been limited to solid alloys or Ferrite. The magnetically soft material becomes magnetized in the direction of an external magnetic field and thus avoids any torque. In accordance with one embodiment of the invention, FIG. 6(*a*) shows an implant 601 that includes a housing 602 containing Ferrofluid, which, as described above, contains tiny magnetic particles suspended in fluid. The housing 602 is sealed to prevent leakage of the Ferrofluid. Similar to a magnetically soft alloy or Ferrite, when a magnetic field is applied to the Ferrofluid, the Ferrofluid is magnetized in the direction of an external magnetic field. Thus, when placed adjacent an external part 604 that includes a magnet 605, the Ferrofluid becomes magnetized and becomes attracted to the magnet 605, holding the external part 604 adjacent the implant 601. FIG. 6(*b*) shows magnetization of an implant 610 that includes Ferrofluid when immersed in an external magnetic field of a MRI scanner. Demagnetization or permanent magnetization in adverse directions is not possible because the Ferrofluid does not assume any sizable permanent magnetization. To obtain a magnetic holding force that is comparable to the case of an implanted permanent magnet, the volume of both the external magnet 605 and the Ferrofluid may have to be comparatively larger.

Figure 7:
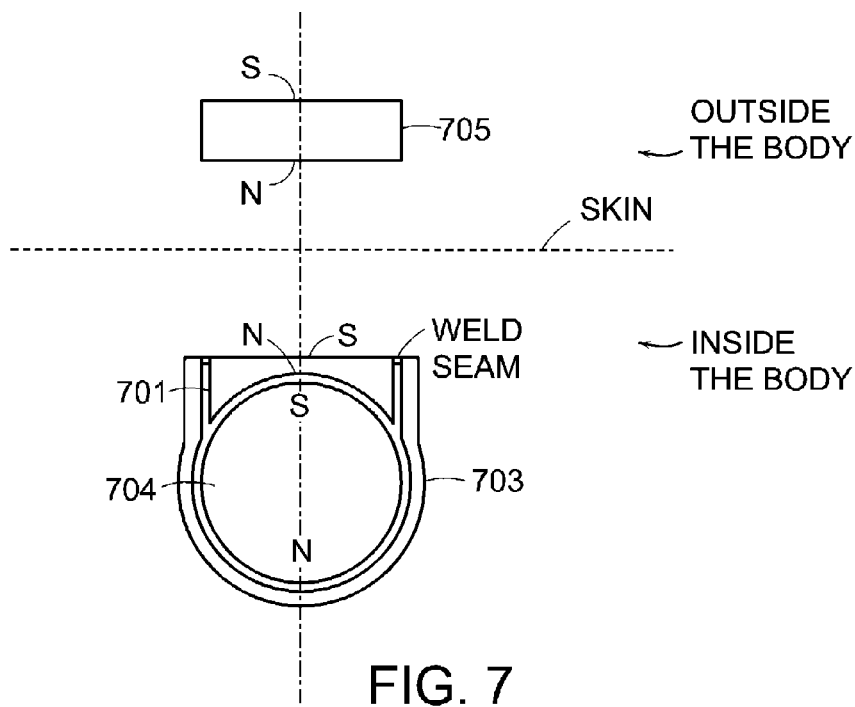
FIG. 7 is a graphical illustration of an implant that includes a spherical magnet and a calotte made of soft magnetic material, in accordance with one embodiment of the invention.

In accordance with another embodiment of the invention, a low-reluctance part may be added to the implant to improve the magnetic flux between the implanted magnet and the external magnet and/or shield magnetic field lines at the implant side facing towards the inner side of the body (i.e. in medial direction)—minimizing magnetic resistance and imaging artifacts, especially near the medial side of the implant. For example, in accordance with one embodiment of the invention, the low-reluctance part is a cylinder 701 with a spherical calotte made of magnetically soft material, as shown in FIG. 7. The cylinder 701 is positioned inside a hermetic encapsulation 703 enclosing an implanted, spherical permanent magnet 704. Instead of a cylinder 701, the low-reluctance part may be a cone, or another shape, with the curvature of the calotte typically being variable and designed to best fit the shape of the permanent magnet 704. The magnetically soft material is magnetized and attracted by the permanent magnet 704. The spherical magnet 704, which can also be variable in shape, may be coated by a thin layer of material to minimize friction, such as Teflon®. In other embodiments, a lubricant may be placed in the small gap between the spherical magnet 704 and the cylinder or cone 701 with spherical calotte. The cylinder 701 provides a path of low magnetic resistance (reluctance) for the magnetic field lines facing towards the magnet 705 of an external device. Additionally, the permanent magnet 704 is attracted to the low-reluctance part 701, preventing small movements (rattling) of the magnet inside its encapsulation 703.

In further illustrative embodiments of the invention, a method and device for preventing induction of excessive voltages in the implant receiver coil/electronics and in the electrode circuit is presented. These excessive voltages may be induced, for example, by RF pulses during an MRI examination.

Figure 8A:
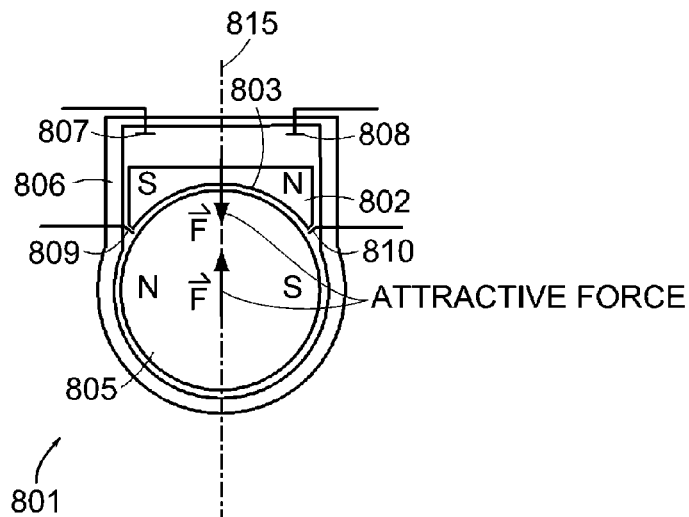
FIG. 8(a) is a graphical illustration of an implant that includes a spherical magnet, a calotte made of soft magnetic material, and a switching function, in accordance with one embodiment of the invention, with no external magnetic field.
Figure 8B:
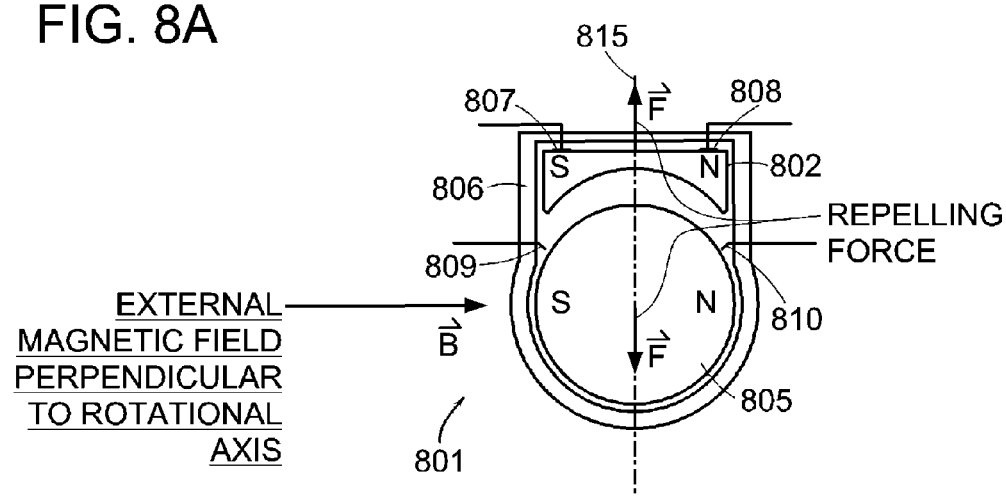
FIG. 8(b) shows the implant of FIG. 8(a) with an external magnetic field perpendicular to the implant's rotational symmetry axis, in accordance with one embodiment of the invention.

In accordance with one embodiment of the invention, an implant 801 having a permanent magnet 805 positioned in a housing 806 includes a switching function, as shown in FIG. 8(*a*). Permanent magnet 805 is free to rotate in response to an external magnetic field, and may be, without limitation, spherical, as shown in FIG. 8(*a*) or cylindrical in shape (see below). The switching function is achieved through use of a low-reluctance part 802 that includes an electrically conductive surface, which may be, without limitation, a conductive coating such as aluminum, nickel, copper, gold and/or silver. The low-reluctance part 802 is free to move towards or away from the permanent magnet 805 so as to open or close at least one pair of electrical contacts 807-810 positioned within the housing 806. Low-reluctance part 802 may vary in shape, including, without limitation, a cylinder with a spherical calotte 803 having a curvature designed to best fit the shape of permanent magnet 805.

Positioning of low-reluctance part 802, and thus the switching state of one or more electric contacts 807-810, depends on the presence and the orientation of an external magnetic field, resulting in an attractive or repulsive force between the permanent magnet 805 and the low-reluctance part 802. In the absence of an external magnetic field, as shown in FIG. 8(*a*), the low-reluctance part 802 is attracted by the permanent magnet 805, as this represents the smallest energy level. In the presence of an external magnetic field that is oriented parallel to the implant's rotational symmetry axis 815 as shown in FIG. 8(*c*), the spherical magnet 805 turns to align its magnetic momentum vector with the external magnetic field. The low-reluctance part 802 is thus magnetized along its axis, generating a magnetic dipole parallel to the symmetry axis 815. This results in an attractive force between the spherical magnet 805 and the low-reluctance part 802. Alternatively, an external magnetic field which is oriented normal to the implant's rotational symmetry axis 815, as shown in FIG. 8(*b*), magnetizes the magnetically soft material 802 in a different direction, turning the spherical magnet 805 into a different direction and causing a repulsive force between the spherical magnet 805 and the low-reluctance part 802.

Through the use of electrical contacts 807-810, switching functions can thus be exploited. Based on the external magnetic field, the low-reluctance part 802 is capable of shifting between a first and second position, as described above. In the first position, the electrically conductive surface of the low-reluctance part 802 is in simultaneous contact with a first and a second switching contact 807 and 808 (or alternatively 809 and 810), while in the second position, the electrically conductive surface is out of contact with at least one of the first and second switching contacts 807 and 808 (or alternatively 809 and 810).

Figure 8C:
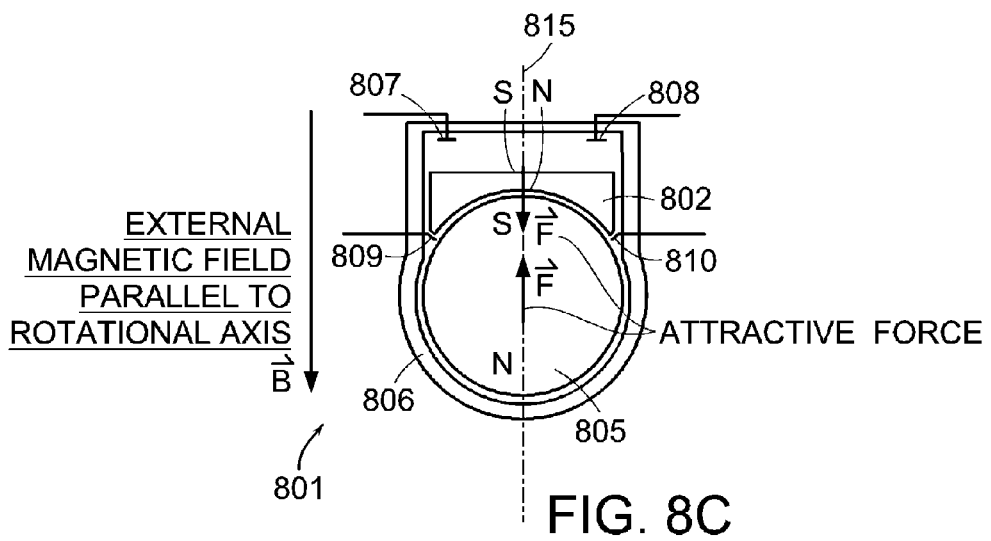
FIG. 8(c) shows the implant of FIG. 8(a) with an external magnetic field parallel to the implant's rotational symmetry, in accordance with one embodiment of the invention.

Dependant on configuration, the above-described switching function can be implemented to close or open electrical circuits based on the presence of a strong external magnetic field oriented at a certain angle to, for example, the rotational symmetry axis of the device. A switching function which opens an electric circuit during the presence of a strong magnetic field perpendicular to the symmetry axis of the embodiment could, for example, be employed to protect receiver circuits of implants during MRI. If the rotational symmetry axis of the device is oriented perpendicular to the main magnetic field $B_0$ in an MR scanner, a component of the circularly rotating magnetic RF field $B_1$ (generated by the MRI unit) is oriented perpendicular to the receiver coil plane (FIG. 8b), allowing induction of (eventually excessive) voltages which may destroy the receiver electronics. An opening switch between the receiver coil and the receiver electronic circuit may be used to protect the receiver electronics. If the rotational symmetry axis of the device is oriented parallel to the main magnetic field $B_0$ in an MR scanner, the switch near the magnet remains closed, as shown in FIG. 8c. Since the magnetic RF field vector $B_1$ is in this case circularly rotating in the receiver coil plane, no voltages can be induced in the receiver circuit. Outside the MR scanner, in the presence of external parts of a cochlear implant system, the external magnet causes a magnetic field in axial direction, and the magnetic switch is closed. In this mode of operation, the voltages which are generated by the external coil of the implant system and which are induced in the implanted coil are passed on to the receiver electronic circuit. The angle between the orientation of the external magnetic field and the rotational symmetry axis of the embodiment at which attraction between the low-reluctance part and the magnet changes into repulsion (i.e. the switching angle) depends on the geometric dimensions of the low-reluctance part.

Figure 9:
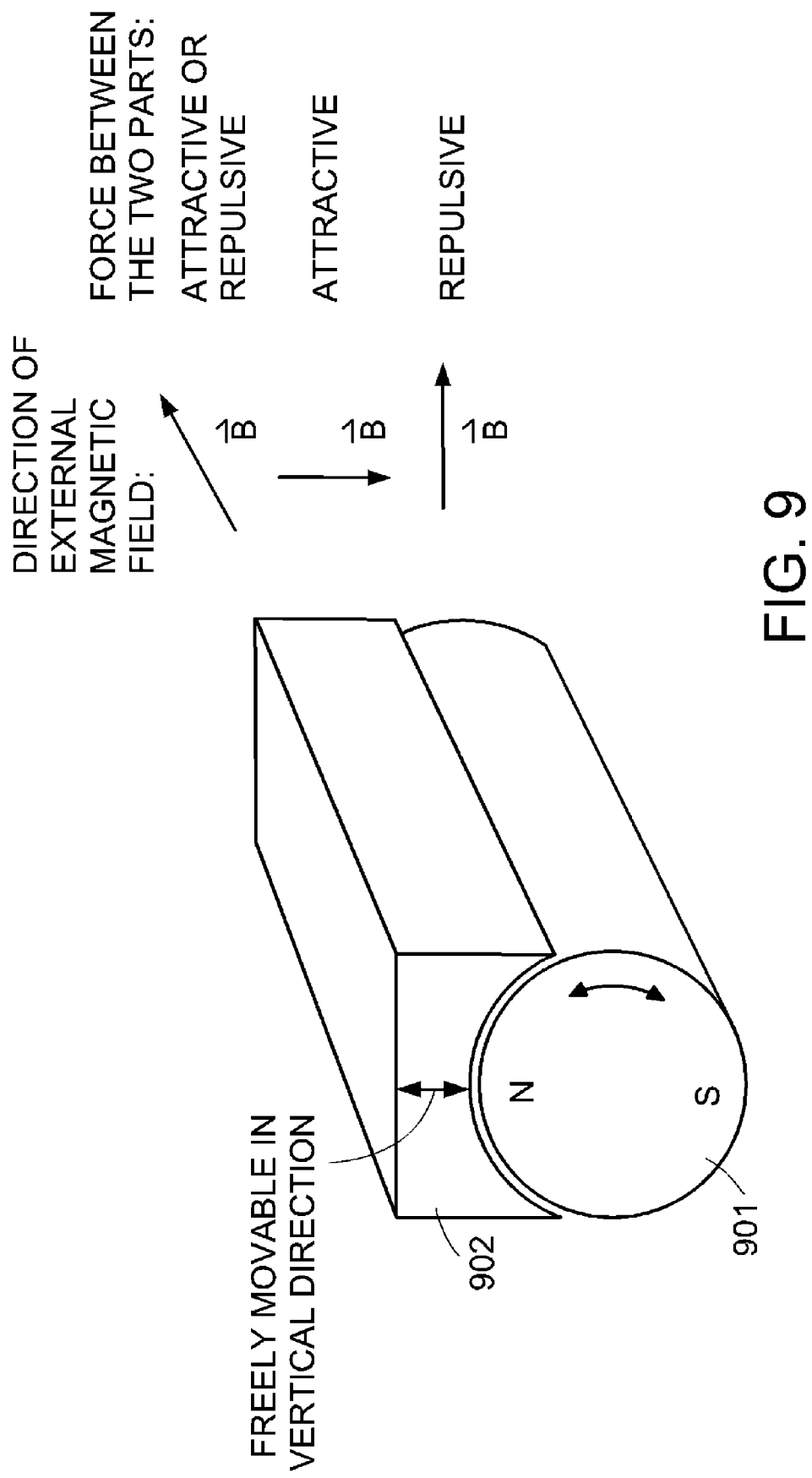
FIG. 9 is a graphical illustration of an implant that includes a cylindrical magnet and a switching function, in accordance with one embodiment of the invention.

Instead of a spherical structure, the permanent magnet 901 may be a cylindrical structure which is free to turn around its rotational axis, as shown in FIG. 9, in accordance with one embodiment of the invention. In such embodiments, the magnetically soft part 902 may be a cuboid with a concave side that fits over the magnetic cylinder 901. Both parts 901, 902 may be encapsulated and the cuboid 902 may be free to move in a vertical direction. A magnetic field orienting in a vertical direction (radially through the cylindrical magnet 901 and vertically through the magnetically soft part 902) would cause an attractive force between the cylindrical magnet 901 and the magnetically soft part 902, whereas a magnetic field orienting in radial direction (horizontally) would cause a repulsive force between the two parts 901, 902. A magnetic field in an axial direction (parallel to the axis of the cylindrical magnet 901) could cause either an attractive or repulsive force, depending on the magnetic properties of the magnetized cylinder 901.

Figure 10:
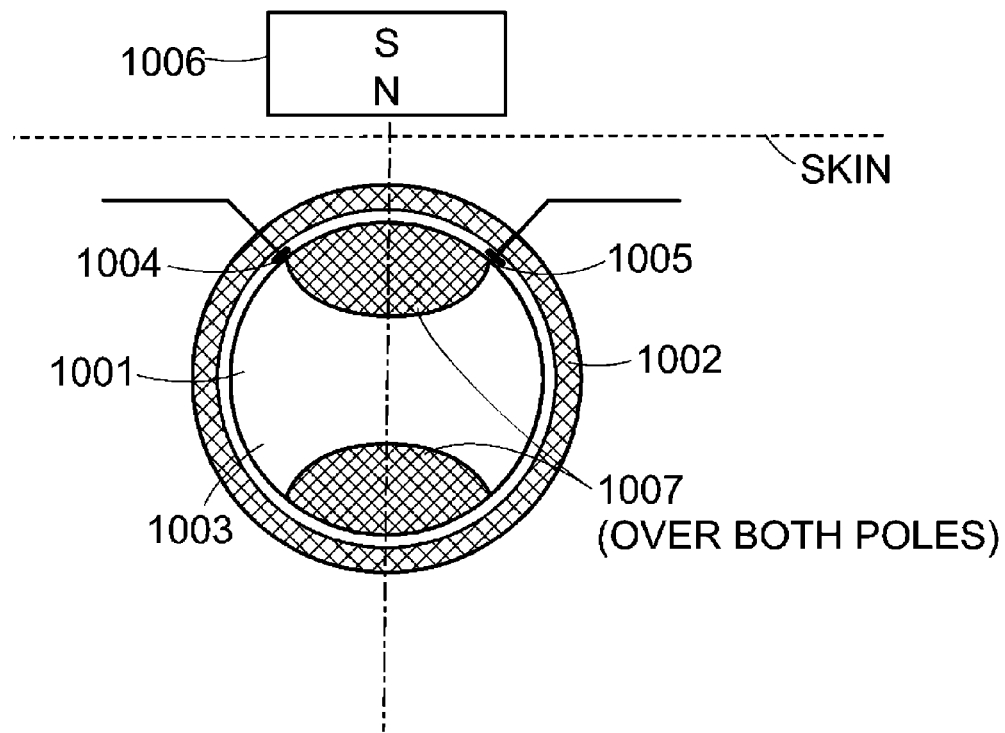
FIG. 10 is a graphical illustration of an implant that includes a spherical magnet and a switching function, in accordance with one embodiment of the invention.

In accordance with another embodiment of the invention, the switch function may include a freely turnable permanent magnet 1001 in a non-magnetic housing 1002, wherein a magnetic soft body is not required, as shown in FIG. 10. Permanent magnet 1001 may be, without limitation, a spherical or cylindrical magnet. The permanent magnet 1001 includes at least one conductive surface 1007 and at least one non-conductive surface 1003. These surfaces 1002 and 1003 may be implemented by coating portions of the magnet 1001 with conductive or non-conductive materials where appropriate. A first switching contact 1004 and a second switching contact 1005 is positioned on the housing 1005. The magnet 1001 is capable of rotating in response to an external magnetic field to a first position, in which the conductive surface is in contact with both the first and second contacts 1004 and 1005, and a second position, in which the conductive surface is out of contact with at least one of the first and second contacts 1004 and 1005.

Depending on the orientation of the spherical magnet 1001, which is defined by the orientation of the external magnetic field, which may be generated by, without limitation, an external magnet 1006 or an MR scanner, different switching functions (opening or closing of circuits) can be implemented. For example, by conductively coating the spherical magnet 1001 over only one magnetic pole, a switching function can be implemented which opens or closes an electric circuit only at a certain angle and orientation of the external magnetic field. By optimizing the geometric form of conducting and non-conducting surface areas of the spherical magnet, and/or by adding more switching contacts, a wide variety of even more complex switching functions (e.g. "make before break") can be defined depending on the orientation of the external magnetic field.

Figure 11:
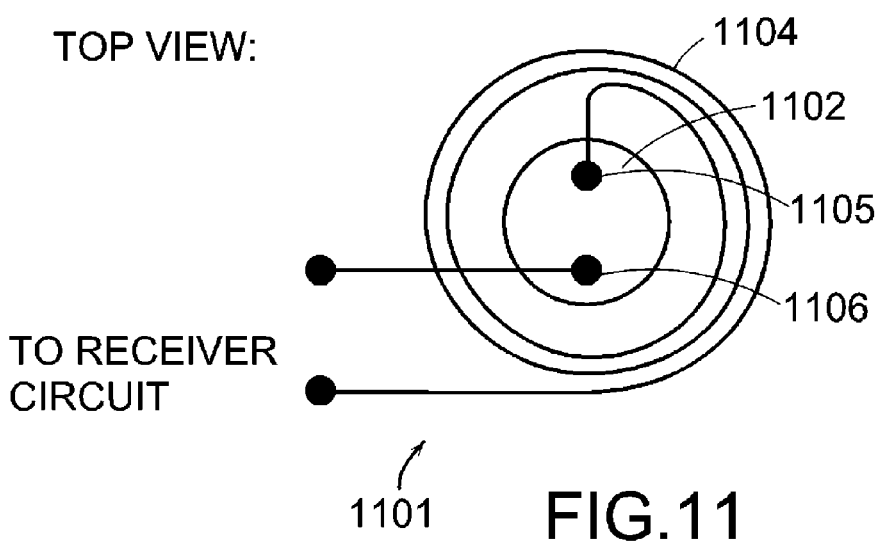
FIG. 11 is a graphical illustration of a top view of an implant that includes a spherical magnet and switching function, in accordance with one embodiment of the invention.
Figure 12A:
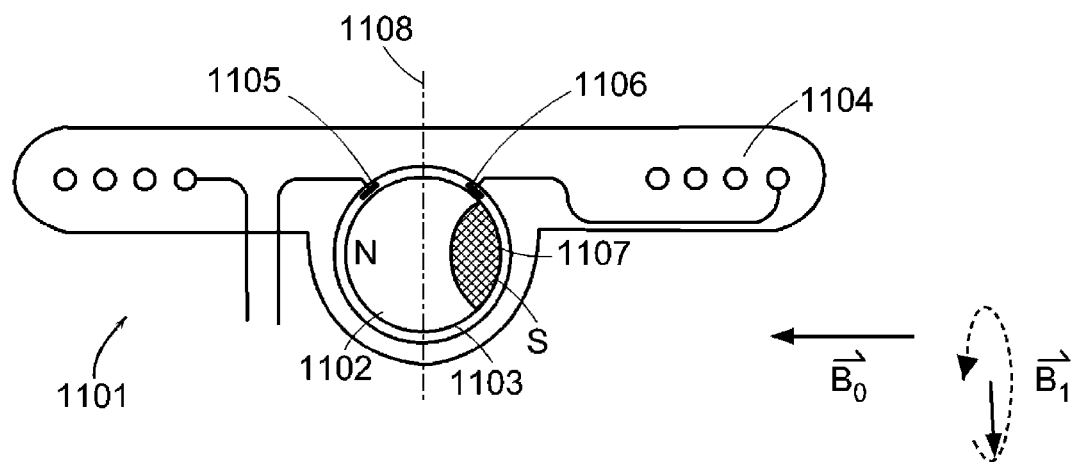
FIG. 12(a) is a graphical illustration of a side view of the implant of FIG. 11 with an external magnetic field orientated perpendicular to the implant's rotational symmetry axis, in accordance with one embodiment of the invention.

In various embodiments, this can be exploited as an overvoltage protection for an implant receiver circuit in an MR scanner. In particular, a switching function between the implant's receiver coil and the implant's receiver electronic circuit can be implemented so as to protect the receiver electronics. In accordance with one embodiment of the invention, FIG. 11 shows a top view of an implant 1101, such as, but not limited to a cochlear implant, that includes a spherical magnet 1102 encapsulated in a housing 1103 (see FIG. 12(a)). The implant further includes a receiver coil 1104, coupled to a first switching contact 1105 and a second switching contact 1106. Referring now to FIG. 12(a), which is a side view of the implant 1101 of FIG. 11, the coil 1104 is positioned in a plane and symmetrically coiled around magnet 1102 about an axis 1108. The magnet 1102 includes a conductive surface 1107 positioned on a South pole of the magnet 1102. If the rotational symmetry axis 1108 of the implant 1101 is oriented perpendicular to the main magnetic field $B_0$ in an MR scanner, a component of the circularly rotating magnetic RF field $B_1$ is oriented perpendicular to the receiver coil 1104 plane, allowing possible induction of (eventually excessive) voltages in the coil which could destroy the implant's 1101 electronics. However, the spherical magnet 1102 rotates in response to the external magnetic field such that the electrically conductive surface 1107 of the magnet 1102 does not contact either switching contact 1105 and 1106, preventing excessive voltages to be passed to the receiver circuitry.

Figure 12B:
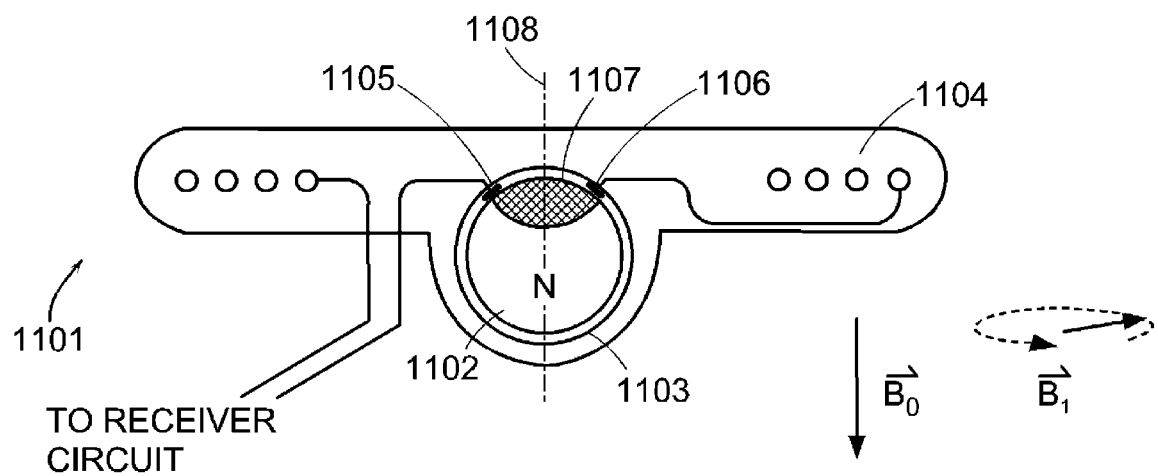
FIG. 12(b) is a graphical illustration of a side view of the implant of FIG. 11 with an external magnetic field orientated parallel to the implant's rotational symmetry axis, in accordance with one embodiment of the invention.

If the rotational symmetry axis of the implant 1101 is oriented parallel to the main magnetic field $B_0$ in an MR scanner, the magnet 1102 is orientated such that the electrically conductive surface 1107 of the magnet 1102 contacts both switching contacts 1105 and 1106, and the switch remains closed, as shown in FIG. 12(b). Since the magnetic RF field vector $B_1$ is, in this case, circularly rotating in the receiver coil 1104 plane, no voltages can be induced in the receiver circuit. Outside the MR scanner, in the presence of external parts of a cochlear implant system, the external magnet causes a magnetic field in the axial direction, and the magnetic switch is closed. In this mode of operation, the voltages which are generated by the external coil of the implant system, and which are induced in the implanted coil 1104, are passed on to the receiver electronic circuit.

A switching function may be also implemented by means other than by electrical/mechanical switching contacts. For example, switching could also depend on different optical properties of the magnet or its surface.

Figure 13:
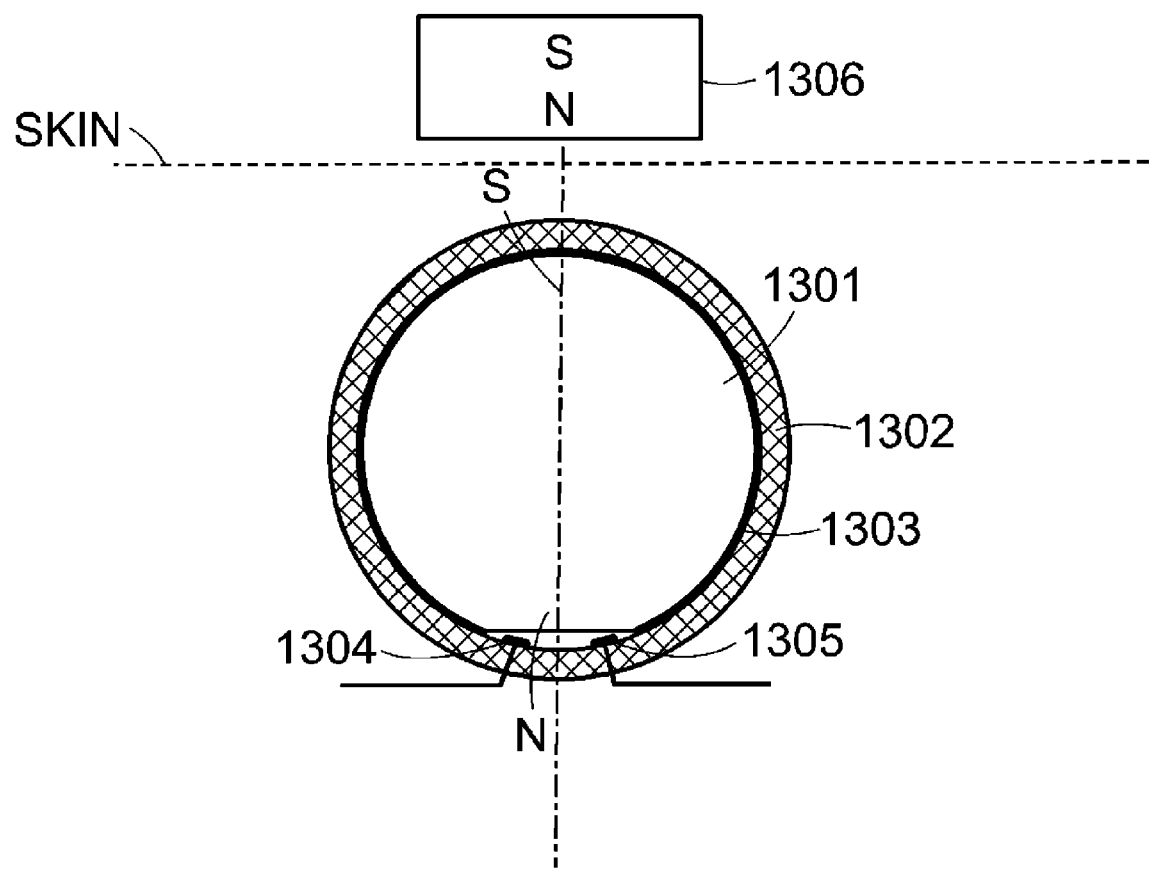
FIG. 13 is a graphical illustration of an implant that includes a spherical magnet and a switching function, the magnet having a recess, in accordance with one embodiment of the invention.

In accordance with one embodiment of the invention, the switching function is accomplished by a freely turnable permanent magnet 1301 in a housing 1302, wherein the magnet 1301 is partly recessed and/or grooved, as shown in FIG. 13. By recessing a portion of magnet 1301, such as at one magnetic pole or between magnetic poles, and by coating at least the non-recessed portion of the magnet 1301 with a conductive material 1303, a switching function depending on the angle and the orientation of the external magnetic field from, for example, an external magnet 1306 can be implemented. In the embodiment shown in FIG. 13, the recessed region is positioned at the north pole of magnet 1301. Accordingly, switching contacts 1304 and 1305 make contact with the conductive coating of magnet 1301 and are closed, unless an external magnetic field is oriented parallel to axis 1306 and towards the skin, whereupon magnet 1301 is orientated such that the recessed region is positioned adjacent switching contacts 1304 and 1305. In various embodiments in which the recessed region of the magnet cannot contact the switching contacts, the entire magnet may be coated with conductive material. Similar to above-described embodiments, magnet may be, without limitation, a spherical or cylindrical magnet. Housing 1302 may hermetically seal the magnet 1301.

Figure 14A:
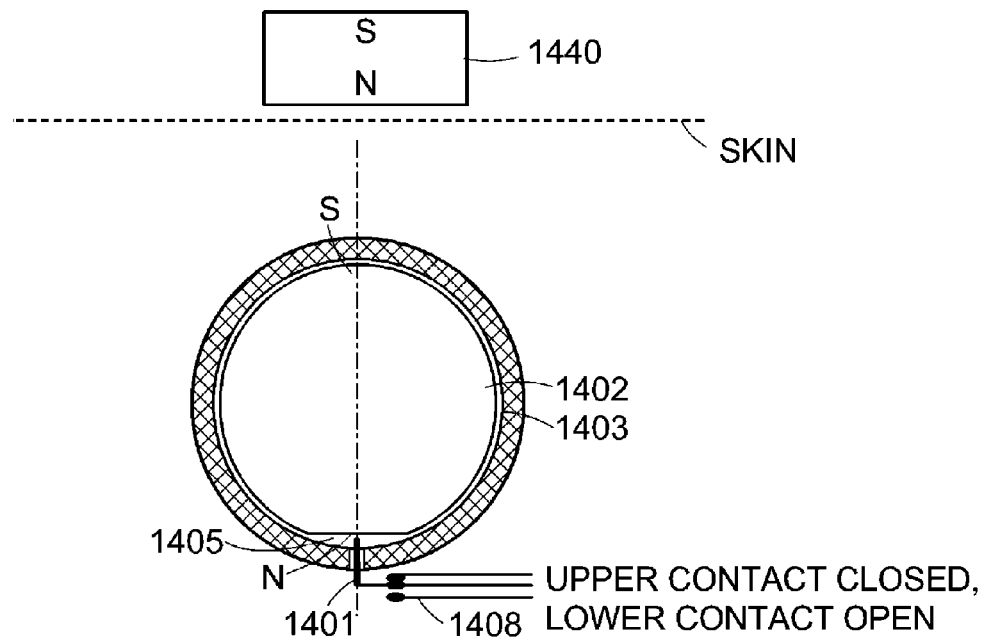
FIG. 14(a) is a graphical illustration of an implant that includes a spherical magnet and a switching function, the magnet having a recess, with an external magnetic field orientated parallel to the implant's rotational symmetry axis of the device such that the pin is not driven, in accordance with one embodiment of the invention.
Figure 14B:
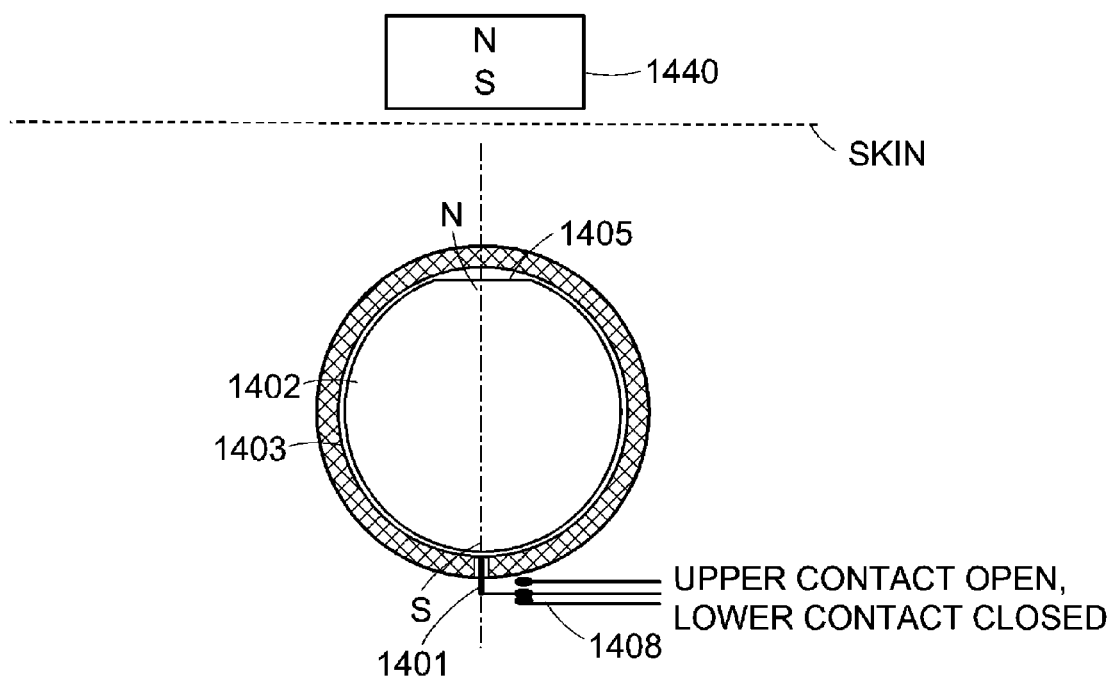
FIG. 14(b) is a graphical illustration of an implant that includes a spherical magnet and a switching function, the magnet having a recess, with an external magnetic field orientated parallel to the implant's rotational symmetry axis of the device such that the pin is driven, in accordance with one embodiment of the invention.

As shown in FIGS. 14(*a*) and 14(*b*), switching may also be accomplished by a pin 1401 which, depending on the orientation of the permanent magnet 1402 and the magnet's geometrical shape at the pin's location, drives a spring contact 1408, in accordance with one embodiment of the invention. Magnet 1402, which may be encapsulated in a housing 1403 and may be hermetically sealed, includes at least one recessed region 1405. Recessed region 1404 may be positioned, without limitation, at a pole or between poles of magnet 1402. Magnet 1402 is free to move in response to an external magnetic field, which may be generated for example, by an external magnet 1440 or MR scanner. As shown in FIG. 14(*b*), the pin 1401 makes contact with, and is driven by, magnet 1402 when the pin 1401 is not aligned with the recessed region 1404. Alternatively, when the pin 1401 is aligned with the recessed region 1404, the pin 1401 is not driven, as shown in FIG. 14(*a*).

Figure 15A:
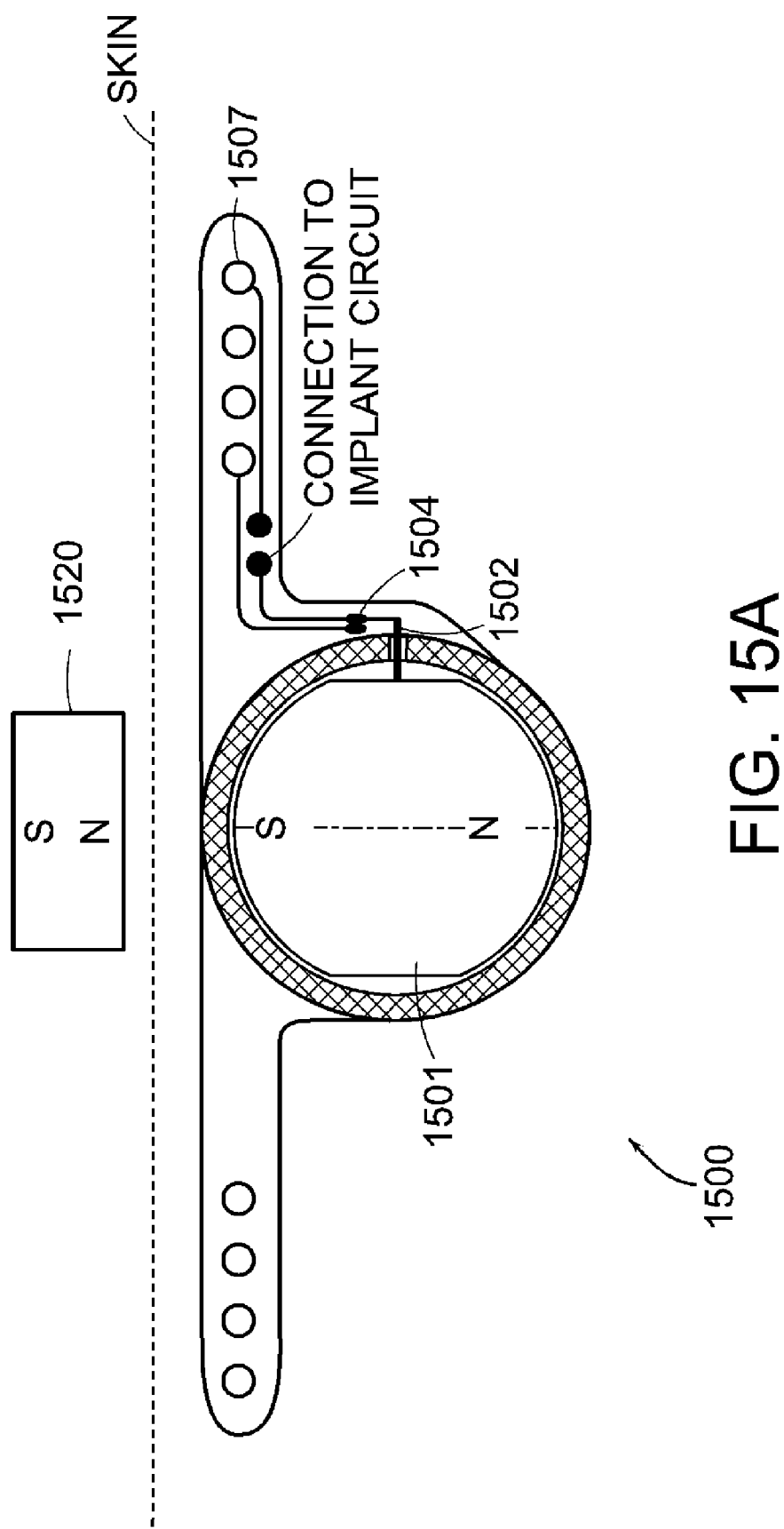
FIG. 15(a) is a graphical illustration of a side view of an implant with a switching function, the implant including a coil and an encapsulated spherical magnet which is recessed at the areas between the two magnet's two poles, with an external magnetic field oriented parallel to the implant's symmetry axis.
Figure 15B:
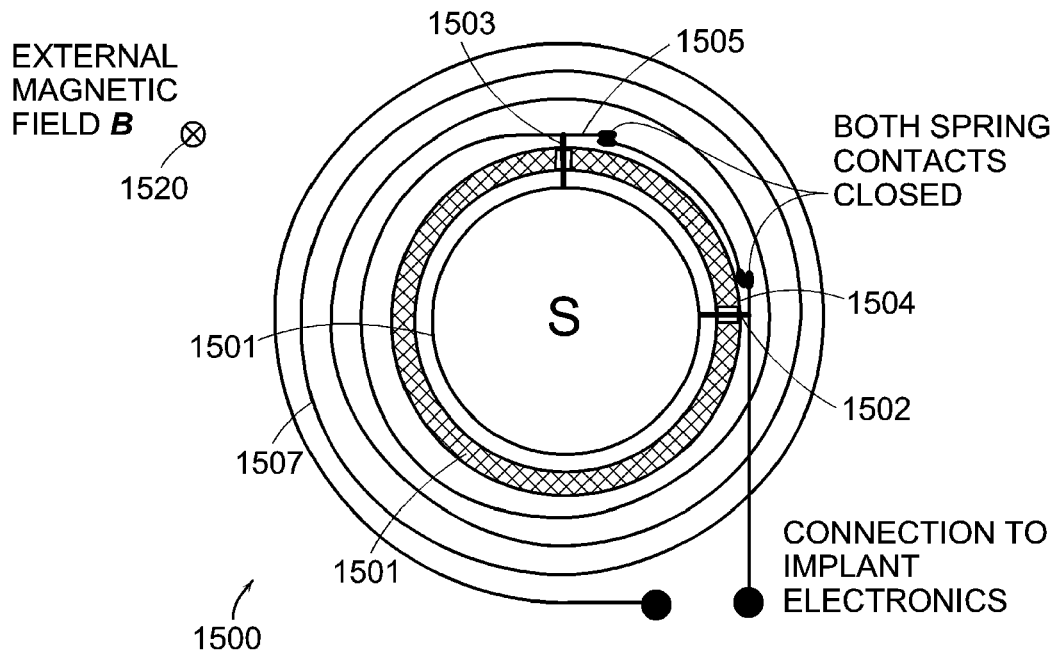
FIG. 15(b) is a graphical illustration of a top view of an implant with a switching function, the implant including a coil and an encapsulated spherical magnet which is recessed at the areas between the magnet's two poles, with an external magnetic field oriented parallel to the implant's symmetry axis.
Figure 15C:
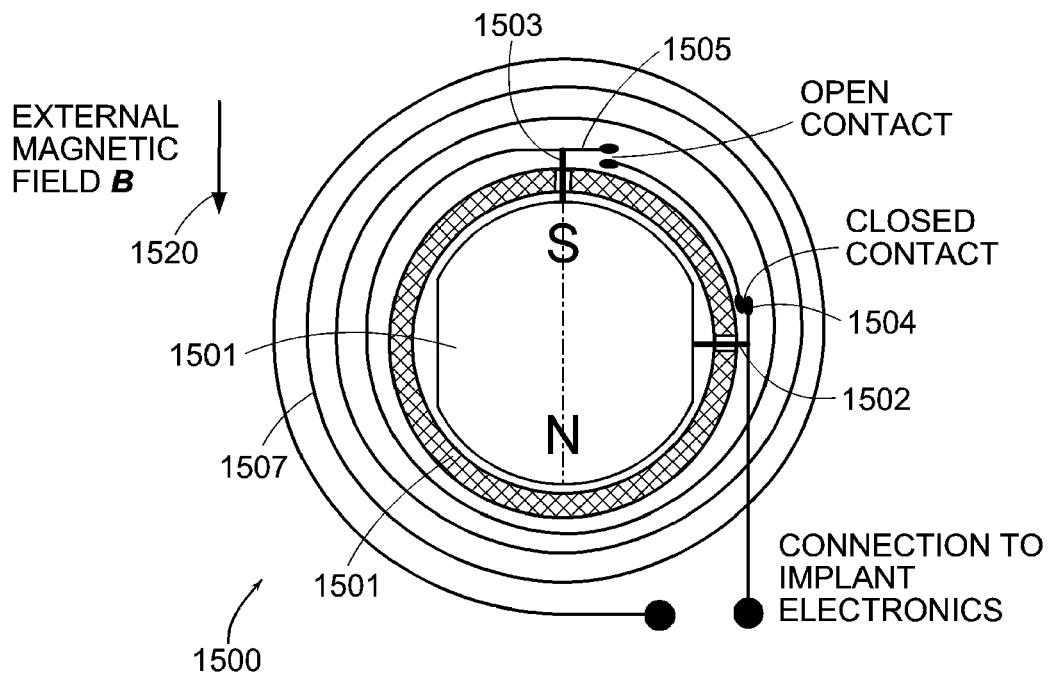
FIG. 15(c) is a graphical illustration of a top view of an implant with a switching function, the implant including a coil and an encapsulated spherical magnet which is recessed at the areas between the magnet's two poles, with an external magnetic field oriented perpendicular to the implant's symmetry axis.

In accordance with another embodiment of the invention, FIGS. 15 (*a-c*) shows an implant 1500 that includes a permanent magnet 1501 that is recessed at an area between the magnet's 1501 two magnetic poles (i.e. at the equator), allowing a switching function based on two pins 1502 and 1503 which drive two spring contacts 1504 and 1505 at the equator. FIG. 15(*a*) is a side view of the implant 1506, while FIGS. 15(*b*) and 15(*c*) show a top view of the implant 1500 when exposed to an external magnetic orientated perpendicular and parallel to the skin surface, respectively. Similar to the embodiment shown in FIG. 12, the implant 1500 requires no additional space in the axial direction and, therefore, allows a slim implant design. In the presence of an external magnetic field oriented parallel to the rotational symmetry axis of the implant 1500 (i.e. perpendicular to the skin), both spring contacts 1504 and 1505 are closed. Implant coil 1507 is connected to the implant electronic circuit, as shown in FIGS. 15(*a*) and 15(*b*). Such a magnetic field may be generated, for example, by an external magnet 1520 associated with the implant system. When the external magnetic field is oriented perpendicular to the rotational symmetry axis of the embodiment (ie. parallel to the skin), as when using an MR scanner, at least one of the two contacts 1504 or 1505 is open, as shown in FIG. 15(*c*). The implant coil 1507 is not connected to the implant electronic circuit. Thus, similar to the embodiment of FIGS. 12(*a*) and 12 (*b*), the implant 1500 can be exploited to protect the coil 1507 and electronic circuit of the implant 1506 during an MRI examination. Note that in order to ensure that the coil 1507 is connected to the implant electronics only when the external magnetic field is oriented parallel to the rotational symmetry axis (ie. perpendicular to the skin), it is necessary to have two switching contacts 1504 and 1505 which are placed in an angle of about 90° against each other. If there was only one switching contact (e.g. the closed contact in FIG. 15*c*), the coil 1507 would be connected to the implant electronics when the external magnetic field is oriented as shown in FIG. 15*c*.

Like for an implant receiver circuit, a switching-function, as described above in accordance with various embodiments of the invention, may also be employed to sufficiently protect an electrode circuit of an implanted stimulator against excessive voltage induction during MRI, if the orientation of the electrode loop plane is known. Electrode circuits may be used, for example, in a cochlear implant to directly stimulate the acoustic nerve.

Additionally, the switching function, as described above in accordance with various embodiments of the invention, may not only be employed to prevent induction of eventually excessive voltages in the implant receiver coil/electronics and in the electrode circuit during an MRI examination, but also for various other reasons which are not limited to MRI examinations. For example, switching functions in an implant could be employed to: switch between a "standard operating" mode and "telemetry" mode of an implant; switch into a mode for re-charging of an implanted battery; de-tune a receiver circuit or to adjust for different receiver frequencies; and optimize RF coupling or power efficiency of an inductive link system.

Furthermore, applications for the magnetically activated switches, as described above in accordance with various embodiments of the invention, is not restricted to the field of medical implants and may be used for implementations other than to avoid induction of potential risks (e.g. torque to the implant magnet, weakening of the implant magnet, induction of excessive voltages in implant circuits) during an MRI examination. The invention could be applied in any area where strong magnetic fields can cause (partial) demagnetization of a permanent magnet or where a hazardous torque is exerted to the magnet. Further, the above-described embodiments of the invention which include electrical switches that are magnetically activated and where the switching state depends on the orientation of the external magnetic field, could be exploited in any other electronic device, whereby receiver coils are switched off by default and can be activated by applying an external magnetic field of a certain orientation.

Additional magnetically sensitive switching elements which may be used to enhance MRI safety of implants, include, but are not limited to: Reed contacts, Hall generators, and Magnetic-field Dependent Resistors (MDR's). The directional sensitivity of these elements may be used with advantage, since in many applications only particular field directions have adverse effects. One advantage that the above-described magneto-switches of the present invention have over REED switches is that the magneto-switches have a switching function at a well-defined angle between the external magnetic field and the symmetry axis of the device. Another advantage that the magneto-switches of the present invention have over Hall generators and MDR's are that they do not require a power supply for switching, since they are passive devices.

The described embodiments of the invention are intended to be merely exemplary and numerous variations and modifications will be apparent to those skilled in the art. All such variations and modifications are intended to be within the scope of the present invention as defined in the appended claims.

What is claimed is:
1. A cochlear implant comprising:
a housing; and
a magnet held by the housing, wherein the magnet is free to turn in any direction without bias and without axial movement.

2. The implant according to claim 1, wherein the magnet is capable of aligning at least partially with an external magnetic field.

3. The implant according to claim 1, further including a lubricant between the housing the magnet.

4. The implant according to claim 1, wherein the magnet is prevented from rattling against the housing.

5. The implant according to claim 1, wherein the magnet is a spherical magnet.

6. The implant according to claim 1, further comprising a first coil adapted to be electromagnetically coupled with a second coil of an external device.

7. The implant according to claim 1, wherein the housing is an encapsulation that hermetically seals the magnet.

8. The implant according to claim 1, wherein the housing includes a magnetically soft material at least partially surrounding the magnet.

9. The implant according to claim 1, wherein the housing includes a material selected from the group of materials consisting of titanium, nonmagnetic stainless steel, and ceramic.

10. The implant according to claim 1, wherein one of the housing and the magnet includes a Teflon surface.

11. The implant according to claim 1, wherein the magnet is coated with a conductive surface.

12. The implant according to claim 1, wherein the magnet is spherically shaped.

13. A cochlear implant comprising:
 a magnet:
 holding means for holding the magnet such that the magnet is free to turn in any direction without bias and without axial movement, wherein the magnet is capable of aligning at least partially with an external magnetic field.

14. The implant according to claim 13, wherein the holding means prevents the magnet from substantially rattling.

15. The implant according to claim 13, wherein the magnet is a spherical magnet.

16. The implant according to claim 13, further comprising a first coil adapted to be electromagnetically coupled with a second coil of an external device.

17. The implant according to claim 13, wherein the holding means includes a magnetically soft material at least partially surrounding the magnet.

18. The implant according to claim 13, wherein one of the holding means and the magnet includes a Teflon surface.

* * * * *